United States Patent
Abraham

(10) Patent No.: US 12,357,651 B2
(45) Date of Patent: Jul. 15, 2025

(54) SYSTEMS AND METHODS FOR USE OF ADENOSINE TRIPHOSPHATE (ATP) TO RELIEVE SYMPTOMS OF COVID-19 AND RELATED INFECTIONS

(71) Applicant: Edward H. Abraham, Hanover, NH (US)

(72) Inventor: Edward H. Abraham, Hanover, NH (US)

(73) Assignee: Adenylate Therapeutics LLC, Claremore, OK (US)

( * ) Notice: Subject to any disclaimer, the term of this patent is extended or adjusted under 35 U.S.C. 154(b) by 78 days.

(21) Appl. No.: 17/314,962

(22) Filed: May 7, 2021

(65) Prior Publication Data

US 2021/0346422 A1 Nov. 11, 2021

Related U.S. Application Data

(60) Provisional application No. 63/021,615, filed on May 7, 2020.

(51) Int. Cl.
*A61K 31/7076* (2006.01)
*A61P 31/14* (2006.01)

(52) U.S. Cl.
CPC .......... *A61K 31/7076* (2013.01); *A61P 31/14* (2018.01)

(58) Field of Classification Search
CPC ............................ A61K 31/7076; A61P 31/14
See application file for complete search history.

(56) References Cited

U.S. PATENT DOCUMENTS

| | | |
|---|---|---|
| 7,148,210 B2 | 12/2006 | Abraham |
| 7,629,328 B2 | 12/2009 | Roberts et al. |
| 7,629,329 B2 | 12/2009 | Lee et al. |
| 7,671,038 B1 | 3/2010 | Rapaport |
| 2004/0116375 A1 | 6/2004 | Abraham |

FOREIGN PATENT DOCUMENTS

WO WO-2021205083 A2 * 10/2021 ............. A61K 31/05

OTHER PUBLICATIONS

English translation of WO2021205083A2, pp. 1-67 (Year: 2021).*
Deftereos et al , The Greek study in the effects of colchicine in COvid-19 complications prevention (GRECCO-19 study): Rationale and study design, Hellenic Journal of Cardiology, published online Apr. 3, 2020, 61: 42-45 (Year: 2020).*
PCT/FR2020/000117 machine translation, 2020, pp. 1-54 (Year: 2020).*
Taghizadeh-Hesary, F. et al., 'The powerful immune system against powerful COVID-19: A hypothesis', Medical Hypotheses, Epub. Apr. 22, 2020, vol. 140, Article No. 109762, pp. 1-3 abstract; p. 2, right column, 4th paragraph.
Cao. Y.-C. et al., 'Remdesivir,• for severe acute respiratory syndrome coronavirus 2 causing COVID-19: An evaluation of the evidence' , Travel Medicine and Infectious Disease, Epub. Apr. 2, 2020, vol. 35, Article No. 101647, pp. 1-6 abstract; p. 4, right column, 3rd paragraph.
Derouiche, S., 'Oxidative stress associated with SARS-Cov-2 (COVID-19) increases the severity of the lung disease—a systematic review', Journal of Infectious Diseases and Epidemiology, May 4, 2020, vol. 6, No. 3, pp. 1-6 the whole document.
Colombo, C. et al., Impact of COVID-19 on people with cystic fibrosis, The Lancet Respiratory Medicine, Epub. Apr. 15, 2020, vol. 8, pp. e35-e36 the whole document.
"International Search Report" for Application No. PCT/US2021/031388, mailed Sep. 1, 2021, 5 pages.
"Written Opinion" for Application No. PCT/US2021/031388, mailed Sep. 1, 2021, 5 pages.
Abraham et al., "A new view of cystic fibrosis through the lens of the COVID-19 pandemic and its implications for COVID-19 therapy in the general population," The Lancet, May 1, 2020, pp. 1-7.
Abraham et al., "COVID-19 versus Cystic Fibrosis Transmembrane Conductance Regulator (CFTR) and ATP," Harvard Library, 2020, pp. 1-12.
Abraham et al., "Cystic fibrosis improves COVID-19 survival and provides clues for treatment of SARS-CoV-2," Purinergic Signalling, 2021, pp. 1-12.
Abraham et al., "Erythrocyte Membrane ATP Binding Cassette (ABC) Proteins: MRP1 and CFTR as Well as CD39 (Ecto-apyrase) Involved in RBC ATP Transport and Elevated Blood Plasma ATP of Cystic Fibrosis," Blood Cells, Molecules, and Diseases, Jan. 2001, vol. 27, Issue 1, pp. 165-180.
Da Silva, et al., High levels of extracellular ATP lead to different inflammatory responses in COVID-19 patients according to the severity, Journal of Molecular Medicine, 2022, 19 pages.
North, R. A., P2X receptors, Philosophical Transactions B, 2016, 371, 7 pages.
Spiess et al., Case Report: Can Inhaled Adenosine Attenuate COVID-19?, Frontiers in Pharmacology, 2021, 12, A673577, 6 pages.
Deftereos et al., Colchicine as a potent antiinflammatory treatment in COVID-19: can we teach an old dog new tricks?, European Heart Journal—Cardiovascular Pharmacotherapy, 6, 255.
Deftereos et al., Effect of Colchicine vs Standard Care on Cardiac and Inflammatory Biomarkers and Clinical Outcomes in Patients Hospitalized With Coronavirus Disease 2019 The GRECCO-19 Randomized Clinical Trial, JAMA Network Open, 2020, 1-14.

* cited by examiner

*Primary Examiner* — Ekaterina Poliakova-Georgantas
(74) *Attorney, Agent, or Firm* — Lewis Rice LLC

(57) ABSTRACT

Treatments for SARS-CoV-2 infection, COVID-19, symptoms of COVID-19, and similar infections. Specifically, treatments for patients identified as having Acute Respiratory Distress Syndrome (ARDS), and specifically COVID-19 ARDS, and/or suffering the effects of hypoxia. The treatments include increasing a patient's naturally occurring levels of ATP, adenosine, and/or other adenosine compounds.

19 Claims, 4 Drawing Sheets

|  | Population | COVID-19 infections | COVID-19 Incidence | COVID-19 deaths | COVID-19 Death Rate |
|---|---|---|---|---|---|
| All Italy | 60,360,000 | 190,000 | 0.003148 | 25,549 | 0.000423 |
| Lombardia, Italy | 10,060,000 | 70,165 | 0.006975 | 12,940 | 0.001286 |
| CF Homozygotes in Lombardia | 825 * | 10 | 0.012100 | 0 | 0.000000 |

\* calculated from CF prevalence in Italy of 8.2 CF/100,000 people in Italy

FIG. 1

| Population | ATP status | Average age | # Patients | # deaths | Death rate (%) |
|---|---|---|---|---|---|
| US, all ages | − ATP | | | | 3.0 ± 2.0 |
| US, age > 70 | − ATP | | | | 11.5 ± 3.5 |
| Facility 2 | − ATP | 82.8 | 12 | 12 | 100 |
| Facility 2 | + ATP | 87.1 | 14 | 0 | 0 |
| Facility 1 | − ATP | 74.7 | 7 | 7 | 100 |
| Facility 1 | + ATP | 68.4 | 25 | 0 | 0 |

Death rates are stratified according to "ATP status," i.e., presence or absence of ATP supplementation. The phrase + ATP indicates patients receiving ATP supplementation while − ATP indicates patients not receiving supplemental ATP. COVID-19-specific death rates for the US general population and US citizens over the age of 70 years are shown for comparison

FIG. 3

| Population | ATP status | Average age | # Patients | # deaths | Death rate (%) |
|---|---|---|---|---|---|
| US, all ages | − ATP | | | | 3.0 ± 2.0 |
| US, age > 70 | − ATP | | | | 11.5 ± 3.5 |
| Facility 3 | − ATP | 81.5 | 22 | 10 | 45.4 |
| Facility 3 | + ATP | 77.9 | 28 | 1 * | 3.5 |

Death rates are stratified according to "ATP status," i.e., presence or absence of ATP supplementation. The phrase + ATP indicates patients receiving ATP supplementation while − ATP indicates patients not receiving supplemental ATP. COVID-19-specific death rates for the US general population and US citizens over the age of 70 years are shown for comparison. * Note that the only patient who died in the supplemental ATP group was diagnosed with COVID-19 on 11 AUG 2020, started on ATP on 13 AUG 2020 and died of COVID-19 shortly thereafter after only 3 doses of ATP

FIG. 4

| Population (%) | ATP status | Average age | # Patients | # deaths | Death rate |
|---|---|---|---|---|---|
| US, all ages | − ATP | | | | 3.0 ± 2.0 |
| US, age > 70 | − ATP | | | | 11.5 ± 3.5 |
| Group 1 | − ATP | 76.7 | 5 | 5 | 100 |
| Group 2 | + ATP | 69.4 | 61 | 0 | 0 |
| Group 2a | + ATP | 67.3 | 34 | 0 | 0 |
| Group 2b | + ATP | 72.0 | 27 | 0 * | 0 * |

Death rates are stratified according to group. Group 1 did not receive supplemental ATP. Group 2 initially had no COVID-19-positive individuals and all members of this group were started on prophylactic supplemental ATP at a low dose rate. Group 2 was subsequently divided into two groups—2a and 2b. Members of group 2a remained free of COVID-19 infection and continued supplemental low dose ATP. Members of group 2b became COVID-19 positive and subsequently received ATP at a higher dose. One member of group 2b died but her death was not attributed to COVID-19 by the facility's staff. She was 84.4 years old and had multiple comorbidities including CHF, bradycardia, DM, hyperlipidemia, acute renal injury, and dementia. She died unexpectedly 32 days after her SARS-CoV-2 formal diagnosis and after completing

FIG. 5

SYSTEMS AND METHODS FOR USE OF ADENOSINE TRIPHOSPHATE (ATP) TO RELIEVE SYMPTOMS OF COVID-19 AND RELATED INFECTIONS

CROSS REFERENCE TO RELATED APPLICATION(S)

This application claims the benefit of U.S. Provisional Patent Application Ser. No. 63/021,615, filed May 7, 2020, the entire disclosure of which is herein incorporated by reference.

BACKGROUND OF THE INVENTION

Field of the Invention

The present disclosure relates to systems and methods for relieving symptoms of COVID-19 and related infections.

Description of the Related Art

In the wake of the 2020 COVID-19 (SARS-CoV-2) virus pandemic, the human population saw the global spread of a deadly disease leading to mass "social distancing" in an attempt to halt its spread. Social distancing was effectively a lighter form of quarantine where all individuals were intended simply to be kept at a distance from each other so that COVID-19, which was believed to be spread from an infected individual to others primarily by airborne transmission, did not interact. Massive social distancing was not an easy program. It caused major economic upheaval, a modification in the operation of human society, and much anxiety.

Social distancing was utilized to combat the spread of COVID-19 for many reasons, but one of the primary was that it one of the few tools that was even available. As those infected with COVID-19 were believed able to transmit the disease many days prior to exhibiting symptoms, every person was a potential carrier and there was no way to limit protective measures only to those that were infected. The virus was believed to primarily be transmitted from one to the other via infected air. Thus, respiratory guards such as surgical masks and later simple cloth face coverings became the norm to avoid viruses that may have been suspended in air from small particles expelled by one effected during a sneeze, cough, or even simple breathing. However, it was discovered relatively early on that the virus could survive on surfaces for many hours or even days depending on the nature of the surface. Hard non-porous surfaces, for example, were found to still have live viruses over a week after the surface had had any contact with an infected individual.

No two viruses or pathogens are the same and the ability of viruses to mutate can result in an ongoing battle to locate, identify, and destroy them. However, many viruses that afflict humans, and particularly those that utilize airborne transmission, are dangerous not due to the pathogen directly, but that such viruses commonly get into the human respiratory system. The human body's response to the virus then often results in respiratory distress including the generation of excess mucus in the respiratory system along with inflammation which can lead to coughing, nasal symptoms such as congestion (rhinitis) and runny nose (rhinorrhea), headaches, and general weakness from the body's reduced capacity to handle air.

In most originally healthy people, the response to virus infection, and even COVID-19, is not so sufficient as to be dangerous, but for those with certain pre-exiting conditions, respiratory symptoms of virus infection can require hospitalization and mechanical ventilation. Ventilators can allow the person to live through the time they are afflicted by the disease by artificially bypassing the natural human processes which are afflicted. Specifically, mechanical ventilators force more oxygen into the lungs than would be obtained by an afflicted patient's normal breathing (and removes carbon dioxide) so that the body's natural oxygen uptake systems have raw materials to work with. Ventilators are designed, in a general sense, to avoid hypoxia and related body shutdown caused by hypoxia. Mechanical ventilation, however, is not without its own risks. The process is unnatural and requires hospitalization and sedation. This presents increased risk that the patient can expose others to the pathogen and requires sufficient ventilators to be available for use.

Particularly with regards to COVID-19, people in the normal population around the world were dying at an alarming rate. Particularly, the elderly, and those with certain co-morbidities often related to breathing issues seemed to be dying at dramatically increased rates. For the most ill of the population, a shortage of ventilators and skilled support staff lead to triage of those individuals who got therapy and those who received palliative care only. While increased production and availability of ventilators can alleviate some of this, it is not the whole story.

There has also been a stark realization that a majority of COVID-19 patients who end up on a ventilator are never successfully weaned and die on the ventilator. This is particularly concerning because it appears to indicate that temporary mechanical ventilation designed to deal with a specific and generally temporary inability of the body to obtain oxygen are not succeeding in that purpose. That has led to postulation that the respiratory distress due to COVID-19 may not actually be confined to oxygen uptake in the lungs, but may also cause loss of function within oxygen processing or transport by other components of the body. One possibility is that COVID-19 infection not only hinders oxygen uptake by the lungs directly (possibly due to the body's response to the infection), but may cause damage to red blood cells reducing their ability to transport oxygen within the body. This result is consistent with mechanical ventilation being ineffective as it is supplies raw material to a system no longer able to process it.

Cystic fibrosis is a progressive genetic disease where gene mutations cause the mucus of the body to be overly thick. Specifically, the cystic fibrosis transmembrane conductance regulator (CFTR) gene causes the CFTR protein to either not be produced or to be produced in an ineffective form. This then means that the body is unable to effectively move chloride to the cell surface resulting in less water being attracted to the cell surface. This results in mucus which is thick and sticky. This thick mucus can then not be effectively cleared by cilia in lung tissue resulting in difficulty obtaining oxygen from the lungs and reduced lung function. Another side effect of thickened mucus in the lungs is that bacteria and viruses often remain in the lungs longer resulting in an increased likelihood of infection. This should make those with cystic fibrosis at increased risk of COVID-19 infection while their already decreased lung function would be expected to result in an increased death rate.

The cystic fibrosis gene mutation has been isolated from the dental and skeletal remains of stone-age Europeans using modern DNA analytic tools, demonstrating that the cystic fibrosis mutation probably extends far into distant antiquity. Until the mid-twentieth century most cystic fibrosis homozygous individuals expired in infancy, making cystic fibrosis a homozygous lethal genetic disease. Any possible benefits of the cystic fibrosis genes were thus conferred to the surviving heterozygous cystic fibrosis populations.

Carla Colombo et al in the Lancet paper entitled "The Impact of COVID-19 on People with cystic fibrosis", the entire disclosure of which is herein incorporated by reference, presents important information about the homozygous cystic fibrosis population in the hot spot of COVID-19 in Lombardia, Italy as well as elsewhere in Europe. While the paper does not offer detailed mechanisms about COVID-19 interaction with cystic fibrosis individuals, it does offer statistical information. This statistical information is illustrated in FIG. 1 showing that the incidence of clinically detectable COVID-19 resulting from COVID-19 infections in Italian cystic fibrosis individuals appears to be 1.73 times higher than in the non-cystic fibrosis population in Lombardia. This is as expected. However, while the incidence of cystic fibrosis is higher, COVID-19 specific mortality in the Italian cystic fibrosis-homozygous population is lower, and specifically, appears to be zero.

At present, there is a lack of detailed information about COVID-19 interactions with the heterozygous cystic fibrosis population. However, these data would indicate that cystic fibrosis heterozygotes will have an increased incidence of COVID-19 but decreased mortality from COVID-19 compared to the general population. While the details of these findings may change with the rapid improvements in detection and calculated exposure based on blood antibody titers and other assays, current cystic fibrosis data seems to suggest an increased risk of contracting COVID-19 mitigated by a remarkable probability of surviving the illness following exposure. This is quite surprising, as airway complications are a hallmark of cystic fibrosis and a major aspect of both morbidity and mortality in cystic fibrosis.

SUMMARY OF THE INVENTION

The following is a summary of the invention in order to provide a basic understanding of some aspects of the invention. This summary is not intended to identify key or critical elements of the invention or to delineate the scope of the invention. The sole purpose of this section is to present some concepts of the invention in a simplified form as a prelude to the more detailed description that is presented later.

Because of these and other problems in the art, the underlying morbidity of COVID-19 and related viral infections may not be of hypoxia caused by decreased effectiveness of oxygen uptake in the lungs, but may be one of total body energy depletion and specifically depletion of blood pools of ATP.

There is, therefore, disclosed herein, among other things, treatments for SARS-CoV-2 infection, COVID-19, symptoms of COVID-19, and similar infections. Specifically, treatments for patients identified as having Acute Respiratory Distress Syndrome (ARDS), and specifically COVID-19 ARDS, and/or suffering the effects of hypoxia. The treatments include increasing a patient's naturally occurring levels of ATP, adenosine, and/or other adenosine compounds.

There is described herein, among other things, a method of treating symptoms of SARS-CoV-2 infection comprising: administering to a COVID-19 positive patient an effective amount of adenosine triphosphate (ATP) to decrease the signs and symptoms of COVID-19.

In an embodiment of the method, the ATP is administered orally.

In an embodiment of the method, the ATP is administered on a first day of treatment in an amount of about 400 to about 800 mg, increased on a second day of treatment to about 1200 mg to about 1600 mg and increased on each subsequent day by about 800 mg per day up to 4000 mg per day.

In an embodiment the method further comprises administering a P2x7 blocker for patients where the signs and symptom include experiencing cytokine storm.

In an embodiment of the method, the signs and symptoms include COVID-19 Acute Respiratory Distress Syndrome (ARDS).

In an embodiment of the method, the signs and symptoms include hypoxia.

In an embodiment of the method, the ATP is administered intravenously.

There is also described herein, in an embodiment, a method of treating symptoms of SARS-CoV-2 infection comprising: administering to a COVID-19 positive patient an effective amount of an adenosine derivative to decrease the signs and symptoms of COVID-19.

In an embodiment of the method, the adenosine derivative is administered orally.

In an embodiment of the method, the adenosine derivative is administered intravenously.

There is also described herein, in an embodiment, a method of treating symptoms of SARS-CoV-2 infection comprising administering to a COVID-19 positive patient an effective amount of adenosine triphosphate (ATP) to increase the patient's ATP level to at least 1.5 times a naturally occurring level in the patient.

In an embodiment of the method, the patient's ATP level is increased to at least 2 times a naturally occurring level in the patient.

In an embodiment of the method, the patient's ATP level is increased to at least 2.5 times a naturally occurring level in the patient.

In an embodiment of the method, the patient's ATP level is increased to at least 3 times a naturally occurring level in the patient.

In an embodiment of the method, the ATP is administered orally.

In an embodiment of the method, the ATP is administered on a first day of treatment in an amount of about 400 to about 800 mg, increased on a second day of treatment to about 1200 mg to about 1600 mg and increased on each subsequent day by about 800 mg per day up to 4000 mg per day.

In an embodiment, the method further comprises administering a P2x7 blocker for patients where the signs and symptom include experiencing cytokine storm.

In an embodiment of the method, the signs and symptoms include COVID-19 Acute Respiratory Distress Syndrome (ARDS).

In an embodiment of the method, the signs and symptoms include hypoxia.

In an embodiment of the method, the ATP is administered intravenously.

There is also disclosed herein, in an embodiment, adenosine triphosphate (ATP) for use in the treatment of symptoms of COVID-19.

In an embodiment of the composition, the ATP is formulated for oral administration.

In an embodiment of the composition, the ATP is formulated to be administered on a first day of treatment in an amount of about 400 to about 800 mg, increased on a second day of treatment to about 1200 mg to about 1600 mg and increased on each subsequent day by about 800 mg per day up to 4000 mg per day.

In an embodiment of the composition, the symptoms include COVID-19 Acute Respiratory Distress Syndrome (ARDS).

In an embodiment of the composition, the symptoms include hypoxia.

In an embodiment of the composition, the ATP is formulated for intravenous administration.

There is also disclosed herein, adenosine derivatives for use in the treatment of symptoms of COVID-19.

In an embodiment of the composition, the adenosine derivatives are formulated for oral administration.

In an embodiment of the composition, the adenosine derivatives are formulated for intravenous administration.

In an embodiment of the composition, the patient's ATP level is increased to at least 1.5 times a naturally occurring level in the patient.

In an embodiment of the composition, the patient's ATP level is increased to at least 2 times a naturally occurring level in the patient.

In an embodiment of the composition, the patient's ATP level is increased to at least 2.5 times a naturally occurring level in the patient.

In an embodiment of the composition, the patient's ATP level is increased to at least 3 times a naturally occurring level in the patient.

BRIEF DESCRIPTION OF THE DRAWINGS

FIG. 1 provides a selection of cystic fibrosis data from Lombardia, Italy in context of Italian experience with COVID-19.

FIG. 3 illustrates COVID-19 specific death rates in 2 facilities for COVID-19 positive patients who had and did not have ATP supplementation.

FIG. 4 illustrates COVID-19-specific death rates in a third facility for COVID-19 positive patients who had and did not have ATP supplementation.

FIG. 5 illustrates COVID-19-specific death rates in a fourth facility where ATP supplementation was initiated

DETAILED DESCRIPTION OF PREFERRED EMBODIMENTS

Figure 2:
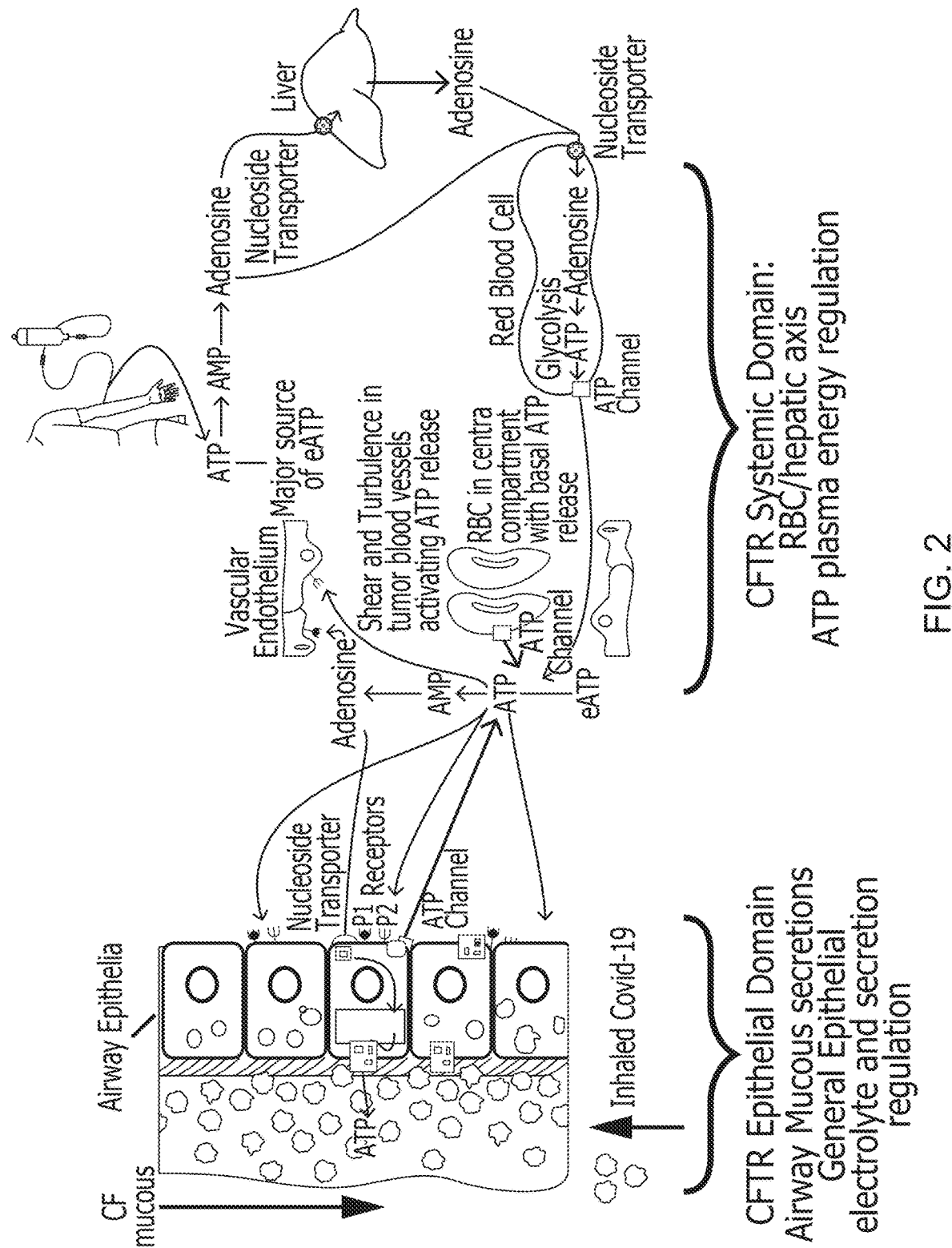
FIG. 2 illustrates CFTR distribution being divided between CFTR in epithelial apical and basolateral membranes and CFTR with systemic distribution: most notably in the erythrocyte membrane.

The following detailed description and disclosure illustrates by way of example and not by way of limitation. This description will clearly enable one skilled in the art to make and use the disclosed systems and methods, and describes several embodiments, adaptations, variations, alternatives, and uses of the disclosed systems and methods. As various changes could be made in the above constructions without departing from the scope of the disclosures, it is intended that all matters contained in the description or shown in the accompanying drawings shall be interpreted as illustrative and not in a limiting sense.

Adenosine Triphosphate (ATP) is an organic compound present in generally every form of life that provides the energy behind many cellular processes. When consumed in metabolic processes, ATP is converted into either adenosine diphosphate (ADP) (which is also known as adenosine pyrophosphate (APP)) or adenosine monophosphate (AMP). ATP is believed to assist with CFTR protein movement on the cell membrane while ADP assists with CFTR protein movement within the cell membrane. ATP is generally regenerated in humans (and other eukaryotes) via glycolysis, citric acid cycle or oxidative phosphorylation, and beta-oxidation. It can occur repeatedly and the human body will typically recycle its own body weight equivalent in ATP each day. While the amount of ATP in any human will typically vary, the amount of ATP in humans will typically decrease with age.

Extracellular ATP is also a potent trigger of cell death (apoptosis and autophagy). Extracellular ATP activates the transcription factor NF-kappa B through activation of the P2Z receptors. The ATP-induced generation of NF-kappa B leads to endothelial cell apoptotic death as discussed in von Albertini, et al. Biochem. Biophys. Res. Commun. 248(3): 822 9 (1998) and von Albertini, et al. 1997 Transplant Proc. 29(1 2):1062. The entire disclosure of both documents is herein incorporated by reference.

Further levels of extracellular ATP and adenosine modulate the immune response; ATP is pro-inflammatory via the P2 receptors of immune cells and extracellular adenosine is strongly anti-inflammatory acting via P1 receptors on immune cells. U.S. Pat. No. 6,436,411, the entire disclosure of which is herein incorporated by reference, also indicates that ATP can activate monocytes or macrophages to induce those cells to produce a number of immune stimulatory molecules including cytokines. U.S. Pat. No. 7,148,210, the entire disclosure of which is herein incorporated by reference, also contemplates treatment of bone metastasis via administration of ATP.

It has previously been determined that (ATP) levels in the blood of patients with cystic fibrosis are at levels which are generally around two times elevated compared to the general population. This may protect cystic fibrosis patients from the most major respiratory effects of COVID-19 and have improved survival compared with non-cystic fibrosis patients. The presence of compounds related to ATP including ADP and AMP may also be elevated and provide the effect.

ATP energy support of COVID-19 patients, or those infected with similarly acting viruses or diseases, will generally support the systemic energy requirements while the patient's immune system is activated. Further, extracellular ATP (eATP) is a potent signal for apoptosis and autophagy which may help target viral laden cells for removal and allow immune cells access to the viral particles. ATP provision may support the infected patient during the time that the immune system is being intrinsically active. Specifically, this disclosure provides an off the shelf approach to treating the systemic manifestations of energy depletion in the elderly and comorbid individuals who have contracted COVID-19.

It should be recognized that throughout this disclosure adenosine or any derivative thereof may be collectively referred to herein as adenosine compounds and that specific reference to any adenosine compound will also provide disclosure of another adenosine compound acting in a known related way. For example, an increase in ATP would be expected to result in an increase in ADP due to the natural cell processing of ATP and vice-versa. Thus, when this disclosure would refer to an increase in ATP in a subject, that increase could be caused by providing ATP directly, or by providing any other adenosine compound whose interaction with natural body activity would result in an increase in ATP or simulate the effects of an increase in ATP.

The mutated CFTR may have resulted in improved survival of the carrier state in the face of prior plagues and epidemics, as there is evidence for cystic fibrosis heterozygous benefit against cholera, typhoid and tuberculosis. Survival benefits have presumably led to the current high prevalence of the CFTR mutation present in the general population (~1/20 individuals).

While cystic fibrosis is associated with increased viscosity of mucous of the airways and other organs, from FIG. 1 it is evident that the thick cystic fibrosis mucous does not impede the SARS-CoV-2 virus from entry into the airway cells or resulting COVID-19. Cystic fibrosis is also associated with abnormal chloride and electrolyte abnormalities, demonstrated by the chloride sweat test and it has been demonstrated that there is an association between cystic fibrosis and abnormal ATP and purine transport. Specifically the CFTR protein is associated with ATP transport to the extracellular surface of epithelial cells. In normal and cystic fibrosis physiology, the level of extracellular ATP is also controlled by CD39 and CD73, which dephosphorylate ATP and produce extracellular adenosine.

Extracellular ATP (eATP) and adenosine control a variety of epithelial functions through interaction with the P1 and P2 purinergic receptors. Extracellular adenosine returns to the intracellular space via adenosine transporters resulting in renewed intracellular ATP and adenylates. ATP blood levels are increased in cystic fibrosis knockout animals as well as in cystic fibrosis patients. There is also a presence of the CFTR protein in the red blood cell membrane. In cystic fibrosis individuals the red blood cell CFTR protein is mutated. There is a correlation between local oxygen concentration and ATP release from the red blood cell.

There has been substantial evidence that infection with Sars-CoV-2 (COVID-19) is associated with blood clotting in lungs, brain and elsewhere. It seems likely that microclots in the lungs will prevent oxygenation of hemoglobin and cause a decrease in PO2. Therefore, treatment with intravenous ATP delivery to these areas of critical need via the CFTR/RBC/ATP delivery complex may be able to save organs. ATP has also been shown to reverse pulmonary artery hypertension. Pulmonary hypertension is also observed in COVID-19 patients who are showing rapid deterioration in their clinical status.

ATP levels in the blood of patients with cystic fibrosis are approximately twice the levels measured in normal individuals. Blood ATP levels decrease monotonically with the normal ageing process and is exacerbated in a variety of disease states. COVID-19 infection is significantly more lethal in older individuals and individuals with a variety of comorbidities. In patients with various solid tumors with depleted ATP levels, ATP can be safely administered as a prolonged infusion replenishing depleted ATP stores in chronically debilitated cancer patients with metastatic treatment refractory disease (Stage IV cancer). Some solid tumors intrinsically expressing purine receptors such as melanomas are largely absent from the cystic fibrosis population. In advanced hormone refractory prostate cancer, purinergic receptors are overexpressed and, as a result, the addition of oral ATP to the palliative agents, such as samarium-153, dramatically reduces the prostate biomarker PSA.

Deterioration of pulmonary, renal, and gastrointestinal epithelia are all caused or affected by COVID-19. Studies applying high dose oral ATP to athletes and advanced cancer patients resulting in improved athletic performance and cancer patient survival. This approach might be promising and easily applied in the setting of COVID-19 infected individuals who are not yet in intensive care. For COVID-19 individuals who are critically ill and require intensive care, intravenous ATP infusion could be applied. ATP therapy could potentially avoid the need for intubation and mechanical ventilation of COVID-19 infected individuals, or improve their effectiveness, and may give time for other agents and the immune system to engage and clear the viral infection.

While patients with cystic fibrosis are apparently not protected from developing COVID-19 infections, it is believed that the elevated blood ATP in cystic fibrosis individuals allows them to survive the infection at a higher rate. This suggests that mimicking the systemic cystic fibrosis state with oral ATP and/or intravenous ATP may spare COVID-19 normal population individuals the need for placement on ventilators and avoid complications of radical treatment and/or death.

In an embodiment, oral ATP may be provided in 400 mg ATP capsules. Patients who have tested positive for SARS-CoV-2 and/or COVID-19 via any available test may be administered a starting dose upon such test being determined to be positive. Alternatively, treatment may be begun when an individual has shown symptoms of COVID-19 infection and/or when an individual has been exposed to a likely infection vector as a preventative measure. Starting dose may be one or two capsules (400-800 mg) on the first day and if tolerated by the individual increased to three to four capsules on the second day (1200-1600 mg). If this is again well tolerated, the amount may continue to be increased by two capsule (800 mg) per day until the patient is taking up to ten capsules (4000 mg) per day.

Capsules will typically be provided two at a time evenly distributed through the day, but that is not required. Therapy will typically continue until the patient is deemed to have no remaining symptoms of COVID-19, for a total period of 14 days from start, until antibody or similar tests determine that the patient's immune system is sufficient to hold off further disease, or until the patient cannot tolerate the ATP or is unable to take oral ATP (for example due to a need for intubation). In the later case, oral ATP may be replaced with intravenous ATP or intramuscular ATP at a similar effective dose level for the duration of treatment. It is widely recognized that IV administration of ATP results in elevated blood levels and IV administration could also be used on all patients if actual ATP levels after oral ATP administration are not what is intended. Once the SARS-CoV-2 has been cleared from the patient, the ATP administration should be reduced and should be discontinued after 1-2 months.

In an embodiment, ATP may be provided to COVID-19 patients experiencing cytokine storm in conjunction with a P2×7 blocker. The P2X7 receptor is an ATP-gated large multi-functional channel and blocking the P2X7 receptor may serve to decrease the cytokine storm seen in a subset of COVID-19 patients. This can serve to keep the putative pathway in check while simultaneously letting these patients experience the systemic benefits of ATP pool replenishment.

In an embodiment, ATP may be provided to COVID-19 patients identified as having Acute Respiratory Distress Syndrome (ARDS), and specifically COVID-19 ARDS, and/or suffering the effects of hypoxia.

FIG. 2 indicates that CFTR distribution can now be divided between CFTR in epithelial apical and basolateral membranes and CFTR with systemic distribution: most notably in the erythrocyte membrane. The former distribution modulates epithelial secretions including airway mucous and sweat duct sweat. The latter helps regulate systemic ATP and energy distribution. Cystic fibrosis individuals have approximately twice the RBC and plasma as the non-cystic fibrosis general population. ATP distribution can be modified via the detailed pathways illustrated for ATP and adenosine before, during, and after continuous intravenous infusions of ATP in humans. The major source of extracellular ATP (eATP) is infused ATP, which is delivering ATP directly into the blood plasma compartment. After a short infusion time, the elevated eATP pools induce higher activities of catabolic ecto-enzymes. At the termination of a continuous intravenous infusion of ATP, the majority of the exogenously administered ATP is sequestered in the erythrocytes and all the eATP has been degraded. It is known that one can safely bring the ATP levels of elderly patients with a variety of Stage IV solid tumors up to the cystic fibrosis plasma and cystic fibrosis RBC ATP levels with significant clinical and laboratory improvements. This is similar to the demographics of the populations faring worst with COVID-19.

Adenosine compounds may be provided individually or in any combination. Representative adenosine derivatives useful in the systems and methods of the invention include, but are not limited to, Adenosine triphosphate (ATP) Adenosine diphosphate (ADP); Adenosine monophosphate (AMP); AMP-PNP; $\alpha,\beta$-methylene ATP; $\beta,\gamma$-methylene ATP; ATP$\gamma$S, and salts or combinations thereof. Adenosine could also be provided or admixed with a source of phosphorous such as, but not limited to, sodium or potassium phosphate solution to provide an adenosine compound.

In different embodiments, the treatments will be to increase ATP levels to at least 1.5 times their naturally occurring level in the patient, to at least 2 times their naturally occurring level, to at least 2.5 times their naturally occurring level, and to at least 3 times their naturally occurring level. The level may also be selected to simulate the ATP level of a similar individual having cystic fibrosis (either heterozygous cystic fibrosis or homozygous cystic fibrosis) or to provide a level corresponding to an expected level of the same or different individual at a younger age. Typically, a human body has about 0.2 moles of ATP, and may have anywhere between about 1 and about 10 micromoles per gram of body tissue weight. The target amounts may be selected, in an embodiment, by testing an individual for their current or a prior ATP level and then administering ATP to reach the target level, or the target level may be selected based on an expected level for individuals with similar body characteristics (e.g. gender, age, mass, etc.)

In alternative embodiments, the treatments may not increase ATP directly, but may increase ADP, AMP, or adenosine levels. These levels may also be increased to any value including at least 1.5 time natural level, at least 2 times natural level, at least 2.5 times natural level, at least 3 times natural level, a level selected to simulate ADP, AMP, or adenosine level of a similar individual having cystic fibrosis, or a level of the same or different individual at a younger age.

Adenosine or any adenosine compound (including without limitation ATP, ADP, and AMP) may be used for the treatment of humans and/or animals with COVID-19 or any similar viral infection, including domestic, sport, laboratory, and farm animals. It may also be provided to those exposed or potentially exposed to the SARS-CoV-2 virus even if they have not yet developed COVID-19 or COVID-19 symptoms as a preventative measure. It is contemplated that if the Adenosine or adenosine compound is to be administered directly, it may be obtained from any source, including from yeast fermentation in any process including being done purposefully for such generation or as a by-product of other fermentation processes such as the brewing of beer. It may also be obtained from human or non-human animal donors. It may be purified as necessary from the generation process. ATP may also be provided to a human patient indirectly through the provision of a non-adenosine compound which causes natural levels of ATP to increase to sufficient amounts, or through application of a mechanical device or medical procedure having the same effect.

The various adenosine components may be formulated into a pharmaceutical composition comprising an effective amount of the component and a pharmaceutically acceptable carrier. An effective amount of each component of the drug combination may be administered to the patient in a manner which, when combined with the other components of the drug combination, ultimately decreases the signs or symptoms of COVID-19 or other infection generating similar signs or symptoms. Beneficial effects of the composition may, for instance, include, for example, at least 50%, at least 75% or at least 100% increase in blood oxidation or a reduction in any effect of hypoxia of at least 50%, at least 75% or at least 100%. The amount of each component and the specific pharmaceutically acceptable carrier will vary depending upon, for example, the component being administered, the patient and the condition of this patient, the mode of administration, and the nature of the severity of the current symptoms being treated.

Pharmaceutically acceptable carriers are materials useful for the purpose of administering the medicament, which are preferably sterile and non-toxic, and may be solid, liquid, or gaseous materials, which are otherwise inert and medically acceptable, and are compatible with the active ingredients.

The pharmaceutical compositions may contain other active ingredients such as preservatives. The pharmaceutical compositions may take the form of a solution, emulsion, suspension, ointment, cream, granule, powder, drops, spray, tablet, capsule, sachet, lozenge, ampoule, pessary, or suppository. They may be administered by continuous or intermittent infusion, parenterally, intramuscularly, subcutaneously, intravenously, intraarterially, intrathecally, intraarticularly, transdermally, orally, bucally, as a suppository or pessary, topically, and/or as an aerosol, spray, or drops. Such administration may be accompanied by pharmacologic studies to determine the optimal dose and schedule and would be within the skill of the ordinary practitioners.

Rates of infusion of an adenosine compound may be initially administered intravenously to patients in daily dosages commencing at rates ranging from 25 to 50 µg/kg/min for up to 8 hours. Gradual increments ranging from 25 to 50 µg/kg/min up to a daily maximum of 100 µg/kg/min may be administered for eight hours to determine the maximal therapeutic efficacy and minimum toxicity. For intravenous injection of an adenosine compound, the dose may be about 1 to 100 mg/kg of body weight. The solution may contain antioxidants, buffers, and the like. If applied topically as a liquid, ointment, or cream, the adenosine compound may be present in an amount of about 100 mg to about 500 mg of the composition. For oral administration, the adenosine compound may be administered, for example, as an enterically coated preparation or as a suspension or solution and should be administered in an amount of about 1 to 100 mg/kg of body weight per day. As one of skill in the art may appreciate, oral dose ranges of 25 to 1000 mg may be administered three or four times a day.

Rates of oral administration of an adenosine compound may be initially administered to patients in daily dosages commencing at 20 to 100 mg four times a day. Gradual increments ranging from 20 to 100 mg four times a day may be administered to determine the maximal therapeutic efficacy and minimum toxicity. In other embodiments, doses may be greater or lesser in number.

The adenosine compound may also be formulated for injection and may be presented in unit dose form in ampules or in multi-dose containers with an added preservative. The pharmaceutical composition may take such forms as suspensions, solutions, or emulsions in oily or aqueous vehicles, and may contain formulatory agents such as suspending, stabilizing and/or dispensing agents. Alternatively, the active ingredient may be in powder form for constitution with a suitable vehicle, e.g., sterile, pyrogen-free water, before use.

Alternatively compositions may be applied to the body of the patient as a topical ointment or cream for skin absorption. The adenosine compounds may be presented in an ointment, for instance with a water soluble ointment base, or in a cream, for instance with an oil in water cream base, in a concentration of from about 100 mg/L to 500 mg/L. The compounds may also be applied into body orifices such as the nose and oral cavity in the form of spray or drops. The compositions may also be applied into body orifices such as the rectum and vagina in the form of a suppository or cream.

It should also be recognized that the above can be used in conjunction with other treatments. Specifically, they may be used in conjunction other antiviral agents, including the antiviral agent remdivisir ($C_{27}H_{35}N_6O_8P$). Remdivisir converts intracellularly to its active form which is a structural analog of adenosine. By blocking aspects of the viral RNA transcriptase and ultimately inactivating intracellular viral particles both metabolically and re-productively, the combination of directly supplied adenosine compounds with remdivisir would allow the simultaneous anti-viral activity to proceed while ATP replenishes the depleted patient ATP stores.

The systems and methods above can also be used in conjunction with blood plasma infusion. Infusion of fresh plasma from donors recently recovered from COVID-19 infections improves recovery of COVID-19 recipient patient (as reported in the Boston Globe: by Christopher Gavin, Apr. 22, 2020). Plasma from patients recovered from COVID-19 contains antibodies that can attack the virus and the plasma is intrinsically rich in adenylates but could be further supplemented with ATP to improve the life-saving effectiveness of the infusion. Supplying plasma with ATP supplementation (either to the plasma directly or to the patient) could again perform the role of replenishing depleted systemic ATP stores.

Example 1

FIG. 3 provides a summary of short-term results of a non-randomized trial of ATP supplementation for treatment of COVID-19 at two different residential care facilities. When the facilities experienced a rapid and insidious onset of COVID-19 in 2020, optional oral ATP nutritional supplementation to COVID-19-positive patients in these two facilities was offered. Patients were given free choice to either accept or reject ATP supplementation. ATP doses ranged from 400-mg capsules four times per day (1600 mg) in the younger patients at facility 1 to three 400-mg capsules three times per day (3600 mg) for the older patients in facility 2. In both facilities, ATP was taken for at least a week after confirmation of SARS-CoV-2 infection. ATP also was offered in powder form to be mixed with food or drink at 450 mg per dose.

In facilities 1 and 2, all patients who declined ATP died of COVID-19 while all patients accepting oral ATP were alive and recovering 2 months after the initiation of supplemental ATP. The two initial groups in each facility (presence or absence of ATP supplementation) were comparable in terms of age and comorbidities. From the initial 13 patients diagnosed with COVID-19 in facility 1, six patients with average age 75.0 years chose to start ATP while the remaining seven with average age 74.7 years chose not to take ATP. Because of the visible developing benefit conferred by ATP, all subsequent COVID-19 patients at the facility 1 chose to begin taking ATP at the time of their diagnoses. All six patients who initially chose ATP were still alive.

At facility 2, all of the patients receiving ATP started taking ATP on the same day following confirmation of viral infection. All of the facility 2 patients taking ATP were alive. Because all patients taking ATP were elderly with multiple co-morbidities (including diabetes and heart disease), it would be expected that their death rate should be worse than that of the general population of individuals over 70 years of age.

Example 2

Using a protocol similar to those used in facilities 1 and 2, ATP supplementation was begun in facility 3. In facility 3, all COVID-19 patients taking supplemental ATP survived except for one patient with extenuating circumstances as explained in FIG. 4.

Example 3

A slightly different approach was used in facility 4. In facility 4, all inpatients—regardless of COVID-19 status— were begun on a lower dose of ATP supplementation. This dose was increased in the event of COVID-19 positivity. Thus, while in the prior examples, ATP supplementation was given only to COVID-19-positive patients. In this example, low-level ATP supplementation was offered to all patients. However, the amount of supplemental ATP was increased if subsequent testing confirmed the presence of COVID-19. The findings for this example are provided in FIG. 5

While the invention has been disclosed in conjunction with a description of certain embodiments, including those that are currently believed to be useful embodiments, the detailed description is intended to be illustrative and should not be understood to limit the scope of the present disclosure. As would be understood by one of ordinary skill in the art, embodiments other than those described in detail herein are encompassed by the present invention. Modifications and variations of the described embodiments may be made without departing from the spirit and scope of the invention.

It will further be understood that any of the ranges, values, properties, or characteristics given for any single component of the present disclosure can be used interchangeably with any ranges, values, properties, or characteristics given for any of the other components of the disclosure, where compatible, to form an embodiment having defined values for each of the components, as given herein throughout. Further, ranges provided for a genus or a category can also be applied to species within the genus or members of the category unless otherwise noted.

The qualifier "generally," and similar qualifiers as used in the present case, would be understood by one of ordinary skill in the art to accommodate recognizable attempts to conform a device to the qualified term, which may nevertheless fall short of doing so. This is because terms such as "spherical" are purely geometric constructs and no real-world component or relationship is truly "spherical" in the geometric sense. Variations from geometric and mathematical descriptions are unavoidable due to, among other things, manufacturing tolerances resulting in shape variations, defects and imperfections, non-uniform thermal expansion, and natural wear. Moreover, there exists for every object a level of magnification at which geometric and mathematical descriptors fail due to the nature of matter. One of ordinary skill would thus understand the term "generally" and relationships contemplated herein regardless of the inclusion of such qualifiers to include a range of variations from the literal geometric meaning of the term in view of these and other considerations.

The invention claimed is:

1. A method of treating symptoms of SARS-COV-2 infection consisting essentially of:
orally administering to a COVID-19 positive patient an effective amount of adenosine triphosphate (ATP) to decrease the signs and symptoms of COVID-19.

2. The method of claim 1 wherein said ATP is administered on a first day of treatment in an amount of about 400 to about 800 mg, increased on a second day of treatment to about 1200 mg to about 1600 mg and increased on each subsequent day by about 800 mg per day up to 4000 mg per day.

3. The method of claim 1 further comprising administering a P2×7 blocker for patients where said signs and symptom include experiencing cytokine storm.

4. The method of claim 1 wherein said signs and symptoms include COVID-19 Acute Respiratory Distress Syndrome (ARDS).

5. The method of claim 1 wherein said signs and symptoms include hypoxia.

6. A method of treating symptoms of SARS-COV-2 infection consisting essentially of:
intravenously administering to a COVID-19 positive patient an effective amount of adenosine triphosphate (ATP) to decrease the signs and symptoms of COVID-19.

7. A method of treating symptoms of SARS-COV-2 infection consisting essentially of:
administering to a COVID-19 positive patient an effective amount of adenosine triphosphate (ATP) to increase said patient's ATP level to at least 1.5 times a naturally occurring level in said patient.

8. The method of claim 7 wherein said patient's ATP level is increased to at least 2 times a naturally occurring level in said patient.

9. The method of claim 8 wherein said patient's ATP level is increased to at least 2.5 times a naturally occurring level in said patient.

10. The method of claim 9 wherein said patient's ATP level is increased to at least 3 times a naturally occurring level in said patient.

11. The method of claim 7 wherein said ATP is administered orally.

12. The method of claim 7 wherein said ATP is administered on a first day of treatment in an amount of about 400 to about 800 mg, increased on a second day of treatment to about 1200 mg to about 1600 mg and increased on each subsequent day by about 800 mg per day up to 4000 mg per day.

13. The method of claim 7 further comprising administering a P2×7 blocker for patients where said signs and symptom include experiencing cytokine storm.

14. The method of claim 7 wherein said signs and symptoms include COVID-19 Acute Respiratory Distress Syndrome (ARDS).

15. The method of claim 7 wherein said signs and symptoms include hypoxia.

16. The method of claim 7 wherein said ATP is administered intravenously.

17. The method of claim 6 further comprising administering a P2×7 blocker for patients where said signs and symptom include experiencing cytokine storm.

18. The method of claim 6 wherein said signs and symptoms include COVID-19 Acute Respiratory Distress Syndrome (ARDS).

19. The method of claim 6 wherein said signs and symptoms include hypoxia.

* * * * *